(12) United States Patent
Clarke et al.

(10) Patent No.: US 12,290,496 B2
(45) Date of Patent: May 6, 2025

(54) COMPOUNDS FOR USE IN PREVENTING OR TREATING ATHLETE OVERTRAINING

(71) Applicant: TDELTAS LIMITED, Thame (GB)

(72) Inventors: Kieran Clarke, Oxford (GB); Peter Hespel, Leuven (BE)

(73) Assignee: TDELTAS LIMITED, Thame (GB)

( * ) Notice: Subject to any disclaimer, the term of this patent is extended or adjusted under 35 U.S.C. 154(b) by 708 days.

(21) Appl. No.: 17/282,594

(22) PCT Filed: Oct. 3, 2019

(86) PCT No.: PCT/GB2019/052797
§ 371 (c)(1),
(2) Date: Apr. 2, 2021

(87) PCT Pub. No.: WO2020/070506
PCT Pub. Date: Apr. 9, 2020

(65) Prior Publication Data
US 2021/0338612 A1    Nov. 4, 2021

(30) Foreign Application Priority Data

Oct. 4, 2018 (GB) ..................................... 1816196

(51) Int. Cl.
*A61K 31/19* (2006.01)
*A61K 31/22* (2006.01)
*A61K 31/23* (2006.01)
*A61K 31/765* (2006.01)
*A61P 21/06* (2006.01)

(52) U.S. Cl.
CPC .............. *A61K 31/19* (2013.01); *A61K 31/22* (2013.01); *A61K 31/23* (2013.01); *A61K 31/765* (2013.01); *A61P 21/06* (2018.01)

(58) Field of Classification Search
CPC ........ A61K 31/19; A61K 31/22; A61K 31/23; A61K 31/765; A61P 21/06; A61P 3/00; A61P 9/00; A61P 21/00
See application file for complete search history.

(56) References Cited

U.S. PATENT DOCUMENTS

| | | |
|---|---|---|
| 6,323,237 B1 | 11/2001 | Veech |
| 8,642,654 B2 | 2/2014 | Clarke et al. |
| 2007/0208081 A1 | 9/2007 | Gross |
| 2007/0286916 A1 | 12/2007 | Bengmark |
| 2009/0253781 A1 | 10/2009 | Veech |
| 2011/0237666 A1 | 9/2011 | Clarke et al. |
| 2012/0322719 A1 | 12/2012 | Pavlov |
| 2015/0164855 A1* | 6/2015 | Clarke ............... A61P 21/00 514/460 |
| 2015/0283163 A1 | 10/2015 | Rayburn et al. |
| 2016/0108442 A1 | 4/2016 | Adelstein et al. |
| 2016/0263098 A1 | 9/2016 | Mantzoros |
| 2017/0296501 A1 | 10/2017 | Lowery |
| 2018/0008629 A1 | 1/2018 | Dixit |

FOREIGN PATENT DOCUMENTS

| | | |
|---|---|---|
| GB | 2517088 A | 2/2015 |
| WO | WO2004108740 A2 | 12/2004 |
| WO | WO2006020137 A2 | 2/2006 |
| WO | WO2006020179 A1 | 2/2006 |
| WO | WO2008110034 A1 | 9/2008 |
| WO | WO2009089144 A1 | 7/2009 |
| WO | WO2010021766 A1 | 2/2010 |
| WO | WO2014140308 A1 | 9/2014 |
| WO | WO2014153416 A1 | 9/2014 |
| WO | WO2014190251 A1 | 11/2014 |
| WO | WO2016123229 A1 | 8/2016 |
| WO | WO2017184788 A1 | 10/2017 |
| WO | WO2019002828 A1 | 1/2019 |

OTHER PUBLICATIONS

GB Examination Report dated Jun. 15, 2022 for Application No. GB2105967.0, 3 pages.
Szczepaniak, et al., "Magnetic Resonance Spectroscopy to Measure Hepatic Triglyceride Content: Prevalence of Hepatic Steatosis in the General Population", Am J Physiol Endocrinol Metab, 288:E462-E468, 2005.
Fracanzani, et al., "Risk of Nonalcoholic Steatohepatitis and Fibrosis in Patients with Nonalcoholic Fatty Liver Disease and Low Visceral Adiposity", Author Manuscript, available at http://hdl.handle.net/2318/83956, 24 pp. (subsequently published at Journal of Hepatology, vol. 54, Issue 6, 2011) doi:10.1016/j.jhep.2010.09.037.
Das, et al., "Nonobese Population in a Developing Country Has a High Prevalence of Nonalcoholic Fatty Liver and Significant Liver Disease", Hepatology, 2010:1593-1602.
Kemper, et al., "An Ester of B-Hydroxybutyrate Regulates Cholesterol Biosynthesis in Rats and a Cholesterol Biomarker in Humans", Lipids (2015) 50:1185-1193.
Unknown, "Keto forum: The Best Fatty Liver Diet", 18 pages, downloaded Aug. 15, 2018 from https://www.ruled.me/keto-best-fatty-liver-diet.
Machado, et al., "No. Need for a Large Belly to Have NASH", Journal of Hepatology, 2011, 54:1090-1093.
Margariti, et al., "Non-alcoholic Fatty Liver Disease May Develop in Individuals with Normal Body Mass Index", Annals of Gastroenterology (2012) 25:45-51.
Pavlides, et al., "Multiparametric Magenetic Resonance Imaging Predicts Clinical Outcomes in Patients with Chronic Liver Disease", Journal of Hepatology, 2016, 64:308-315.

(Continued)

*Primary Examiner* — Snigdha Maewall
(74) *Attorney, Agent, or Firm* — FINNEGAN, HENDERSON, FARABOW, GARRETT & DUNNER, LLP

(57) ABSTRACT

The present invention provides a compound for use in preventing or treating overtraining in a subject, wherein the compound is selected from (i) (R)-3-hydroxybutyrate; (ii) an ester of (R)-3-hydroxybutyrate; and (iii) an oligomer obtainable by oligomerising (R)-3-hydroxybutyrate moieties; or a pharmaceutically acceptable salt or solvate thereof.

17 Claims, 9 Drawing Sheets

(56) References Cited

OTHER PUBLICATIONS

Pawlak, et al., "Ketone Body Therapy Protects from Lipotoxicity and Acute Liver Failure Upon Ppara Deficiency", Mol Endocrinol, 2015, 29(8):1134-1143.
Thomas, et al., "Hepatic Triglyceride Content and its Relation to Body Adiposity: a Magnetic Resonance Imaging and Proton Magnetic Resonance Spectroscopy Study", Gut, 2005, 54:122-127.
Frayne, "Metabolic Regulation A Human Perspective", 2d Edition, 2003, pp. 94-96.
Rossi et al., "Suppression of feed intake after parenteral administration of D-B-hydroxybutyrate in pygmy goats", Journal of Veterinary Medicine A, vol. 47, No. 1, 2000, pp. 9-16.
Gibson et al., "Do ketogenic diets really suppress appetite? A systematic review and meta-analysis", Obesity Reviews, 16:64-76 (2015).
Sumithran et al., "Ketosis and appetite-mediating nutrients and hormones after weight loss", European Journal of Clinical Nutrition (2013) 67:759-764.
Johnstone et al., "Effects of a high-protein ketogenic diet on hunger, appetite and weigh loss in obese men feeding ad libitum", Am J Clin Nutr, 87:44-55 (2008).
Paoli et al., "Ketosis, ketogenic diet and food intake control: a complex relationship", Frontiers in Psychology, vol. 6, Article 17, pp. 1-9, 2015.
Chearskul et al., "Effect of weight loss and ketosis on postprandial cholecystokinin and free fatty acid concentrations", Am J Clin Nutr,2008:87:1238-46.
Clarke et al., "Kinetics, safety and tolerability of (R)-3-hydroxybutyl (R)-3-hydroxybutyrate in healthy adult subjects", Regulatory Toxicology and Pharmacology, 63:401-408 (2012).
Chacko et al., "Effect of ghrelin on glucose regulation in mice", Am J Physiol Endocrinol Metab 302: E1055-E1062, 2012.
Stubbs et al., "A ketone ester drink lowers human ghrelin and appetite", Obesity, vol. 26, No. 2, 2018, pp. 29-273.
Pawan et al., "Effects of 3-hydroxybutyrate on obese subjects on very-low-energy diets", The Lancet, Jan. 1983, Elsevier, vol. 321, pp. 15-17.
Srivastava et al., "Mitochondroial biogensis and increased uncoupling protein 1 in brown adipose tissue of mice fed a ketone ester diet", The FASEB Journal; vol. 26, No. 6, 2012, pp. 2351-2362.
GB Search Report dated Mar. 21, 2019, issued in GB Application No. GB1815588.7.
GB Search Report dated May 22, 2018 issued in GB Application No. GB1715654.8.
International Preliminary Report on Patentability dated Mar. 31, 2020, issued in PCT/GB2018/052717, 9 pages.
Wade, A and Weller, PJ, "Handbook of Pharmaceutical Excipients, 2d Edition" 1994.
International Search Report of corresponding PCT/GB2019/052797, dated Jan. 3, 2020, 4 pages.
Cox et al., "Nutritional Ketosis Alters Fuel Preference and Thereby Endurance Performance in Athletes", Cell Metabolism, Cell Press, vol. 24, No. 2, Jul. 27, 2016, p. 256-268, XP029680184.
Holdsworth et al., "A Ketone Ester Drink Increases Postexercise Muscle Glycogen Synthesis in Humans", Medicine and Science in Sports and Exercise, vol. 49, No. 9, Sep. 1, 2017, p. 1789-1795, XP055649184.
Parker et al., "Beta-hydroxybutyrate favorably alters muscle cell survival and mitochondrial bioenergetics", Apr. 1, 2017, Retrieved from the Internet: URL:https://www.fasebj.org/doi/abs/10.1096/fasebj.31.1_supplement.883.7, KP055649476.
Thomsen et al, "Effects of 3-hydroxybutyrate and free fatty acids on muscle protein kinetics and signaling during LPS-induced inflammation in humans: anticatabolic impact of ketone bodies", The American Journal of Clinical Nutrition, vol. 108, No. 4, Oct. 1, 2018, p. 857-867, XP055649308.
Kreher et al., "Overtraining Syndrome: A Practical Guide", Sports Health: a Multidisciplinary Approach, vol. 4, No. 2, Jan. 31, 2012, p. 128-138, XP055649498.
Jacobs et al., "Creatine Supplementation may prevent NAFLD by stimulating fatty acid oxidation", & Joint Annual Meeting of the ASPET/BPS At Experimental Biology (EB); Boston, MA, USA; Apr. 20-24, 2013 vol. 27, Apr. 1, 2013 (Apr. 1, 2013), FASEB Journal, Abstract only. Retrieved from the Internet: URL:https://www.fasebj.org/doi/abs/10.1096/fasebj.27.1_supplement.222.2.
International Search Report and Written Opinion of corresponding PCT/GB2018/051752, dated Oct. 17, 2018, 14 pages.
UK Patent Office Action issued Jan. 27, 2021 in GB Patent Application No. 1815588.7, 5 pgs.
GB Examination Report dated Mar. 21, 2022 for Application No. GB1816196.8, 7 pages.
GB Examination Report dated Mar. 21, 2022 for Application No. GB2105967.0, 7 pages.
Henderson et al. (http://patient info/doctor/steatohepatitis-and-steatosis-fatty-liver (last edited Aug. 31, 2016)) (Year: 2016).
Examination Report for Corresponding European Application No. 18 737 388.1, dated Oct. 26, 2021, 4 pages.
JP Office Action, dated Oct. 10, 2023, for corresponding JP Patent Application No. 2021-518512, 5 pages.
JP Office Action, dated Oct. 10, 2023, for corresponding JP Patent Application No. 2021-518512, 3 pages (English Translation).
Holdworth, D.A., et al., "Medicine and Science in sports and exercise", 2017, vol. 49, No. 9, pp. 1789-1795.
Kreher, J.B., et al., "Sports Health", 2012, vol. 4, No. 2, pp. 128-138.
Examination Report No. 1 for Standard Patent Application, Jul. 4, 2024, 4 pages.
"Strawberry Pineapple Flavour Pre-Exertion Performance Optimizer", Company: Keto Industries, Australia; Brand: Keto Industries Keto Perform, Published May 2018, 3 pages.

\* cited by examiner

* p< 0.05 Ket vs. Plac (group-effect)
# p< 0.05 vs. pre-ex (time-effect)

\* P < 0.05 Ket vs. Plac (group-effect)
\# P < 0.05 vs. pretest (time effect for K groups)
§ P < 0.05 vs. pretest (time effect for P groups)

* P < 0.05 Ket vs. Plac (group-effect)
# P < 0.05 vs. pretest (time effect for K groups)
§ P < 0.05 vs. pretest (time effect for P groups)

* $P < 0.05$ Ket vs. Plac (group-effect)
$P < 0.05$ vs. pretest (time effect for K groups)
§ $P < 0.05$ vs. pretest (time effect for P groups)

§ p< 0.05 vs. pretest (time effect for P groups)

* p< 0.05 Ket vs. Plac (group-effect)
§ p< 0.05 vs. pretest (time effect for P groups)

COMPOUNDS FOR USE IN PREVENTING OR TREATING ATHLETE OVERTRAINING

CROSS-REFERENCE TO RELATED APPLICATION

This application is a U.S. National Phase Patent Application of, and claims priority to and the benefit of International Application Number PCT/GB2019/052797, filed on Oct. 3, 2019, which claims priority to and the benefit of British Patent Application Number 1816196.8, filed on Oct. 4, 2018, the entire contents of all of which are incorporated herein by reference.

FIELD OF THE INVENTION

The present invention relates to compounds for use in treating, and particularly preventing the effects of overtraining in a subject, and to treatment of conditions associated with overtraining. The invention also relates to prophylactic treatment of a subject to avoid or reduce the risk of developing conditions associated with overtraining.

BACKGROUND OF THE INVENTION

Overtraining occurs when a person exceeds their body's ability to recover from strenuous exercise, to the point where performance declines. Overtraining is a common problem in weight training, but is also experienced by runners and other athletes. The specific condition is known as overtraining syndrome (OTS).

OTS represents a systemic inflammatory process with diffuse effects on the neurohormonal axis affecting host immunology and mood. The major symptoms of overtraining can be classified into four categories:

Biochemical—increased cortisol and decreased free testosterone levels
Immunological—increased susceptibility to infection
Physiological—decreased performance, heavy, sore and stiff muscles, weight loss, changes in heart rate
Psychological—feelings of anxiety, restlessness Generally speaking, athletes train to increase performance. Performance increases are achieved through increased training loads. Increased loads are tolerated only through interspersed periods of rest and recovery-training periodization. Overreaching is considered an accumulation of training load that leads to performance decrements requiring days to weeks for recovery. Overreaching followed by appropriate rest may ultimately lead to performance increases. However, if overreaching is extreme and combined with an additional stressor, overtraining syndrome (OTS) may result. OTS may be caused by systemic inflammation and subsequent effects on the central nervous system, including depressed mood, central fatigue, and resultant neurohormonal changes.

There are various hypotheses for OTS, including the following:

Autonomic nervous system: Parasympathetic predominance causes many symptoms of overtraining syndrome
Central fatigue: Increased tryptophan uptake in the brain leads to increased 5-HT centrally and mood symptoms
Glutamine: Decreased glutamine causes immune dysfunction and increased susceptibility to infection
Hypothalamic: Dysregulation of the hypothalamus and hormonal axes cause many symptoms of overtraining syndrome
Oxidative stress: Excessive oxidative stress causes muscle damage and fatigue.

Although each of these hypotheses seems plausible, they do not, individually, account for all of the symptoms of OTS.

To date, treatment of overtraining has often been based on appropriate rest. Some have proposed that relative rest is more appropriate—building up volume of exercise prior to intensity of exercise. The current body of knowledge on the prevention, diagnosis and treatment of overtraining syndrome is discussed in a review article by Meeusen et al published in the Official Journal of the American College of Sports Medicine, 2012, pages 186-205. There is a need for new and effective ways to prevent and treat overtraining effects in a subject.

The present invention utilises exogenous ketone body precursors. It is generally understood that the term "ketone bodies" encompasses three endogenous compounds: D-β-hydroxybutyrate, acetoacetate and acetone. D-β-hydroxybutyrate is otherwise known as (R)-3-hydroxybutyrate, and the latter term will be used hereinafter. Ketone bodies are produced by the liver from fatty acids during periods of low food intake.

Recent advances in exercise physiology have led to a greater understanding of the importance of adequate nutrition during training and competition. High carbohydrate diets and high fat diets have been compared in multiple trials involving athletes and healthy inactive volunteers, with general improvements in maximal athletic performance using diets with higher carbohydrate intake. Given the rapid depletion of skeletal muscle glycogen during prolonged intense exercise and the increased metabolic efficiency of ketone bodies, ketone bodies have been proposed for use before, during and after exercise. Traditional techniques to achieve a controlled physiological ketosis, i.e. starvation or a low-carbohydrate, low protein, high-fat ketogenic diet, failed to achieve ergogenic effects because of their dependency on limited carbohydrate intake. Recently, an exogenous ketone ester (R)-3-hydroxybutyl (R)-3-hydroxybutyrate was developed, which no longer requires reduced carbohydrate intake to achieve increased serum ketone levels similar to a period of prolonged fasting. Acute ingestion of this ketone ester has been shown to improve endurance performance in elite cyclists by altering fuel competition for oxidative respiration (Cox et al; Cell Metab 24: 256-268, 2016).

Dietary exogenous ketones may not only enhance exercise performance acutely, they may also enhance training adaptation to increase performance over time. It has recently been shown that ketones can be considered as an additional stimulus to acute muscle repair via stimulation of muscle protein synthesis post-exercise (Vandoorne et al; Front. Physiol 2017; Vol. 8: Article 310).

Ketone bodies and ketone body esters have been shown to reduce serum cholesterol and/or triglyceride levels. For instance, WO2009/089144 discloses a ketone diet which doubled the plasma β-hydroxybutyrate concentrations in rats. Total serum cholesterol and HDL and LDL levels were significantly lower in the rats fed this ketone diet.

Ketone bodies and ketone body esters have also been shown to have various other uses, such as treatment of muscle impairment or fatigue, and protection from radiation exposure. Some of these compounds have also been shown to have an effect on muscle recovery after exercise. WO2015/018913, for instance, teaches that a ketone body ester can increase skeletal muscle glycogen by decreasing glycolysis. No effects on overtraining were demonstrated.

SUMMARY OF THE INVENTION

The present invention provides, in a first aspect, a compound for use in preventing or treating overtraining in a subject, wherein the compound is selected from:
(i) (R)-3-hydroxybutyrate;
(ii) an ester of (R)-3-hydroxybutyrate; and
(iii) an oligomer obtainable by oligomerising (R)-3-hydroxybutyrate moieties;
or a pharmaceutically acceptable salt or solvate thereof.

Also provided, in a second aspect of the invention, is a pharmaceutical composition for use in preventing or treating overtraining in a subject, comprising a compound as defined in the first aspect of the invention, and optionally one or more pharmaceutically acceptable excipients.

In a third aspect of the invention there is provided a nutritional composition for use in preventing or treating overtraining in a subject comprising a compound as defined in the first aspect of the invention, and optionally further comprising water and optionally one or more of a flavouring, a protein, carbohydrate, sugars, fat, fibre, vitamins and minerals.

In a fourth aspect of the invention there is provided use of a compound as defined in the first aspect of the invention or a composition according to the second or third aspect of the invention in the manufacture of a medicament for use in preventing or treating overtraining in a subject.

In a fifth aspect of the invention there is provided a method of preventing or treating overtraining in a subject comprising administering to the subject a compound as defined in the first aspect of the invention or a composition according to the second or third aspect of the invention.

Compounds as defined herein provide an exogenous source of ketone to the subject, and have been shown to be effective in the prevention and treatment of overtraining. The compounds used in this invention provide clear beneficial effects in the prevention and treatment of musculoskeletal and hormonal dysregulations induced by overtraining, and can protect against muscle damage. Although the use of ketone esters to reduce muscle breakdown during a single bout of intense exercise was known from WO2015/018913, it would not have been expected that a ketone ester would work consistently to prevent or treat overtraining, specifically decrease OTS.

BRIEF DESCRIPTION OF THE FIGURES

FIG. 6 shows the results of DXA scanning before and after the 3-week training period.

DETAILED DESCRIPTION OF THE INVENTION

Figure 1:
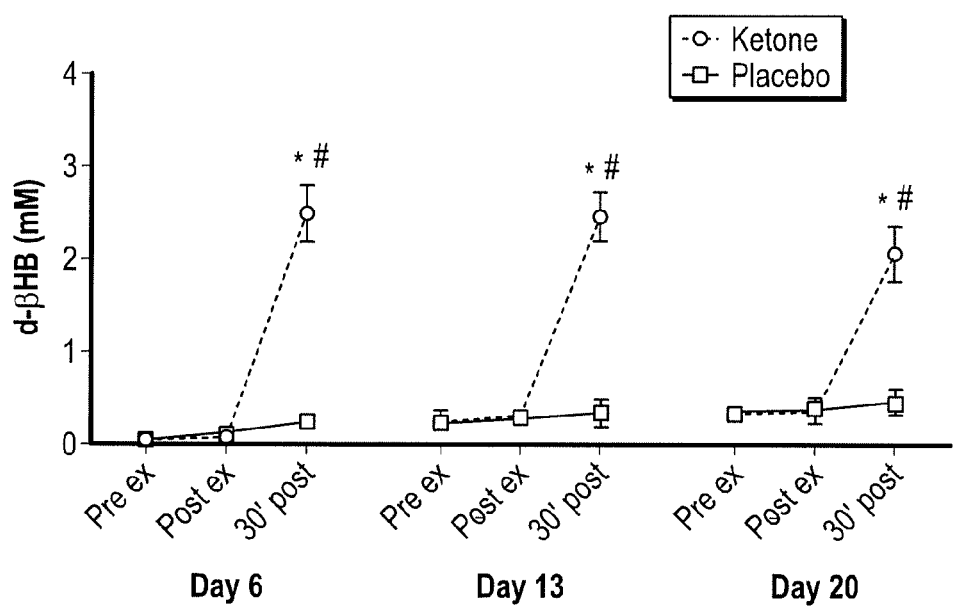
FIG. 1 shows the ketone ((R)-3-hydroxybutyrate) levels on days 6, 13 and 20 before exercise, immediately after exercise and 30 minutes following ingestion of 25 g of ketone ester.

The compounds of the invention provide a source of (R)-3-hydroxybutyrate in the body of the subject. Accordingly, the compound may be (R)-3-hydroxybutyrate itself, or a precursor to (R)-3-hydroxybutyrate, such as an ester or oligomer thereof, which can be broken down in the body to form (R)-3-hydroxybutyrate.

(R)-3-hydroxybutyrate is a ketone body, as defined in "Metabolic Regulation: A Human Perspective" by K N Frayn.

WO2004/108740 discloses that ketone bodies may be administered directly to subjects to achieve elevated levels of ketone bodies. However, direct administration can be difficult and risky under certain circumstances, and the use of esters has therefore been proposed as a preferred alternative. The manufacture of ketone esters has been disclosed, for instance, in WO2014/140308, which describes processes for producing (R)-3-hydroxybutyl (R)-3-hydroxybutyrate.

An ester of (R)-3-hydroxybutyrate can be produced via a transesterification reaction of ethyl-(R)-3-hydroxybutyrate with an alcohol. This reaction may be enzyme catalysed. For instance, an ethyl ester of (R)-3-hydroxybutyrate and (R)-1,3-butanediol may be reacted together in the presence of immobilized lipase under mild vacuum to remove the resultant ethanol by-product.

In a preferred embodiment of the invention, the ester of (R)-3 hydroxybutyrate is a compound of general formula I:

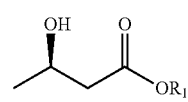

wherein
$R_1$ is a $C_1$-$C_6$ alkyl group, which alkyl group carries up to five —$OR_2$ substituents,
wherein $R_2$ represents hydrogen, or $C_1$-$C_6$ alkyl or wherein —$OR_2$ represents a (R)-3-hydroxybutyrate moiety; or
$R_1$ is a moiety derived from an alcohol $HOR_1$, wherein said alcohol is a sugar.

Typically, zero, one or two —$OR_2$ groups represent a (R)-3-hydroxybutyrate moiety. Preferably, only zero or one —$OR_2$ groups represent a (R)-3-hydroxybutyrate moiety.

Preferred compounds of the invention are esters, particularly those as outlined in formula I above. The $R_1$ moiety is derived from a corresponding alcohol HO—$R_1$. Alcohol HO—$R_1$ may be, for instance, a mono-alcohol, a diol, a polyol, or a sugar.

Preferably, in formula I, $R_1$ is a $C_1$-$C_6$ alkyl group substituted with 0, 1, 2, 3, 4 or 5 —$OR_2$ substituents. Most preferably, $R_1$ is a $C_1$-$C_6$ alkyl group substituted with 1, 2 or 3 —$OR_2$ substituents, typically 1 or 2 —$OR_2$ substituents.

Preferably, $R_2$ is H.

Preferably, $R_1$ has formula —$CH_2$—CH(OH)—$CH_2$(OH) or —$CH_2$—$CH_2$—CH(OH)—$CH_3$. In these cases, $R_1$ is a moiety derived from an alcohol HO—$R_1$, which corresponds to butanediol and glycerol respectively. The butanediol may be racemic 1,3 butanediol. Most preferably, the alcohol HO—$R_1$ corresponds to R-1,3 butanediol. In this case the group $R_1$ is of formula:

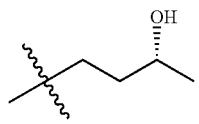 [SMILES: *CC[C@@H](C)O]

Preferably, the compound of the invention is a monoester, i.e. in cases where the alcohol HO—$R_1$ comprises more than one pendant hydroxyl, only one of these reacts to form a hydroxybutyrate moiety. Partial esters are compounds wherein the alcohol HO—$R_1$ comprises more than one pendant hydroxyl, and not all of these have reacted to form a hydroxybutyrate moiety.

A particularly preferred compound of the invention is (R)-3-hydroxybutyrate (R)-1,3-butanediol monoester, otherwise known as (R)-3-hydroxybutyl (R)-3-hydroxybutyrate, of formula:

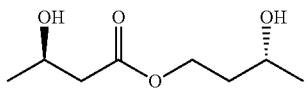

A further preferred compound of the invention is (R)-3-hydroxybutyrate-glycerol partial ester, i.e. (R)-3-hydroxybutyrate-glycerol monoester or diester.

In a different embodiment of the invention, $R_1$ is derived from an alcohol $HOR_1$, wherein said alcohol is a sugar. The sugar may be selected from altrose, arabinose, dextrose, erythrose, fructose, galactose, glucose, gulose, idose, lactose, lyxose, mannose, ribose, ribulose, sucrose, talose, threose, and xylose.

In cases where $R_1$ is derived from an alcohol $HOR_1$ which is a polyol, the polyol may be selected from glycerol, ribitol and xylitol.

In an alternative embodiment of the invention, the compound of the invention is of formula II:

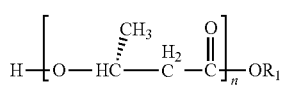

wherein
$R_1$ is as defined above in the first aspect of the invention; and
n is an integer of from 2 to 100.

Preferably, n is from 2 to 50, for instance, 2 to 20, 2 to 10 or 2 to 5. The oligomer may for instance comprise just 2, 3, 4 or 5 repeating units (n=2, 3, 4 or 5). The oligomer may be linear or cyclic in nature.

When the compounds of the invention contain a chiral centre in addition to that depicted in the formulae above, the compounds may be present as racemic mixtures or pure enantiomeric forms.

Compounds of the invention may be present as physiologically compatible salts. For instance, sodium, potassium, calcium or magnesium salts thereof, may be employed.

We have found that (R)-3-hydroxybutyrate-R-1,3-butanediol monoester and (R)-3-hydroxybutyrate-glycerol partial esters provide high circulating levels of (R)-3-hydroxybutyrate in the blood. Furthermore, these esters provide a surprisingly high level of uptake in the gut, thereby enabling high blood concentrations of (R)-3-hydroxybutyrate to be achieved upon consumption of a drink.

Accordingly, in a preferred embodiment, the invention provides a hydroxybutyrate ester or partial ester, for example (R)-3-hydroxybutyrate butane-1,3-diol monoester and (R)-3-hydroxybutyrate glycerol partial ester for use in preventing or treating overtraining in a subject.

Particularly advantageous is (R)-3-hydroxybutyl-(R)-3-hydroxybutyrate as it allows a large rise in blood (R)-3-hydroxybutyrate to be achieved with oral ingestion of a smaller volume of material than with racemic ketones. A subject ingesting the material prior to, or during physical exercise, is more readily able to ingest adequate ketone in order to provide a physiologically beneficial response without risk of physical discomfort (due to for instance ingestion of a large volume of liquid, or a bitter/otherwise aversive flavour). The high level of blood (R)-3-hydroxybutyrate concentration also raises (R)-3-hydroxybutyrate concentrations for a longer period than ketone salts. A lower frequency of doses is then required to maintain raised (R)-3-hydroxybutyrate levels. This also facilitates compliance of the subject with dosing regimens.

The invention relates to the prophylaxis, treatment and recovery of overtraining in a subject, particularly a subject suffering from overtraining syndrome. Prevention of overtraining may be regarded as a subset of treating overtraining, in the sense that the invention relates to treating a subject who is already on the pathway to suffering from overtraining, but is not necessarily showing any overt symptoms thereof.

Compounds used in the invention can be administered to a subject to inhibit, or delay the onset of overtraining in a subject. For instance, the compounds can delay the onset of overtraining symptoms in subjects by at least one day, preferably at least 2, 3, 4, 5 or 6 days, more preferably at least one week, typically at least 2 weeks or at least 3 weeks, compared to subjects who have not received the compound. The compounds can delay and/or reduce the intensity of the symptoms of overtraining. The beneficial effects increase as the duration of the training overload increases in conjunction with administration of compounds of the invention.

Compounds defined herein can also be used to decrease the loss of endurance performance typically associated with overtraining. For instance, the compounds have been shown to increase the power of subjects during prolonged endurance exercise and reduce the loss of power associated with overtraining.

Administration of the compounds of the invention to a subject can treat the effects of overtraining in a subject. By this, we mean any of the physiological, psychological, immunological or biochemical alterations associated with overtraining in a subject.

For instance, a subject who is starting to show signs of overtraining can exhibit a lower peak heart rate during intense exercise. The compounds of the invention have been shown to reduce this lowering of the peak heart rate. Similarly, the submaximal heart rate can be lowered as overtraining develops. The compounds of the invention have been shown to reduce this lowering of the submaximal heart rate.

Furthermore, the compounds of the invention have been shown to increase bone mineralisation, despite an extreme training load. Accordingly, compounds of the invention can be used to increase or maintain bone mass during prevention or treatment of overtraining.

By overtraining, we mean a subject presenting with underperformance during training for several days to weeks. The subject will typically have exceeded their body's ability to recover from strenuous exercise. The overtraining may be minor or extreme. At the minor end of the spectrum, the subject may have undergone overreaching, for instance, "functional overreaching"—a short-term overreaching resulting from increased training leading to a temporary performance decrement (improved performance to follow after rest).

Alternatively, the subject may have undergone "non-functional overreaching"—a longer-term overreaching resulting from intense training leading to a longer performance decrement (full recovery would still follow after rest); accompanied by increased psychological and/or neuro-endocrinological symptoms.

At the more extreme end of the spectrum the subject may be presenting with overtraining syndrome (OTS). Overtraining syndrome is consistent with extreme non-functional overreaching but with (1) longer performance decrement (>2 months), (2) more severe symptoms and maladapted physiology (psychologic, neurologic, endocrinologic, immunologic systems), (3) and an additional stressor not explained by disease.

Diagnosis of OTS is clinical and accomplished through history, which should demonstrate the following: (1) decreased performance persisting despite weeks to months of recovery, (2) disturbances in mood, and (3) lack of signs/symptoms or diagnosis of other possible causes of underperformance.

Hormones such as leptin, adiponectin and ghrelin, as well as hormones such as interleukin-6 and tumour necrosis factor-alpha, have been recently investigated as possibilities for the monitoring of overtraining (von Duvillard S. et al; *Metabolism*. 2011; 60:335-50). Levels of the hormone leptin typically decrease when a subject enters an overtrained state. Administration of a compound as described herein can reduce, delay or inhibit the decrease in leptin levels associated with overtraining. For instance, administration of a compound as defined herein can ensure that leptin levels in a subject remain within 50%, preferably within 40% or 30%, more preferably within 20%, 15% or 10%, most preferably within 5% of their baseline levels in a subject who is overtrained. Administration can also ensure that levels of leptin return to their baseline levels more quickly during recovery from overtraining.

The baseline levels of the subject refer to the subject's average plasma leptin reading, taken before the subject has entered the overtrained state. A typical plasma leptin reading for a man is 2.65-20.7 ng/mL. A typical plasma leptin reading for a woman is 4.7-46 ng/mL.

Noradrenaline levels have been found to be elevated from a subject's baseline levels, when a subject enters the overtrained state. Administration of a compound as described herein can reduce, delay or inhibit the increase in noradrenaline levels associated with overtraining. For instance, administration of a compound as defined herein can ensure that noradrenaline levels in a subject remain within 50%, preferably within 40% or 30%, more preferably within 20%, 15% or 10%, most preferably within 5% of their baseline levels in a subject who is overtrained. Administration can also ensure that levels of noradrenaline return to their baseline levels more quickly during recovery from overtraining.

The baseline levels of the subject refer to the subject's average nocturnal urine noradrenaline reading, taken before the subject has entered the overtrained state. A typical urine noradrenaline reading is <170 μg/24 h (<1005 nmol/d).

Compounds of the invention can also stimulate training adaptation. The compounds increase training volume/quality while at the same time inhibiting overreaching, which ultimately leads to greater training adaptation and improved performance.

Subjects of the invention are typically athletes. The subjects have typically reached a stage of "overtraining" as defined above, and may be suffering from overtraining syndrome. The athlete may have suffered overtraining as a result of intense exercise or training overload (for instance, running, cycling, swimming and/or weight training), without sufficient rest.

Typically, the subject will have been training for several weeks, for instance, at least 1, 2, 3, 4, 5 or 6 weeks, to reach the stage of overtraining.

In order to prevent or delay the onset of overtraining, a subject may ingest the compound of the invention in a prophylactic manner. By this, we mean that the subject may ingest the compound on a regular basis (for instance, every morning, or before bedtime), before any symptoms of overtraining develop. The subject may ingest the compound more than once a day—for instance, twice or three times per day. Alternatively, (or as well as), the subject may ingest the compound before, during and/or after every training session, with or without a carbohydrate and/or protein-based drink.

In a different embodiment of the invention, compounds of the invention are ingested when the symptoms of overtraining have started to develop, as detailed above.

Suitably the compound of the invention, preferably (R)-3-hydroxybutyrate-(R)-1,3-butanediol monoester, is ingested at a level of at least 100 mg per kilogram of body weight of ketone per day. Desirably, the ketone body or ketone body ester is ingested at a level adequate to provide a blood plasma ketone level of at least 0.1 mM, preferably at least 0.2 mM, more preferably at least 1 mM and optimally at least 2 mM. Suitably the ketone body or ketone body ester is ingested at a level such that the blood plasma ketone level does not exceed 20 mM, suitably does not exceed 10 mM or 8 mM and may not exceed 5 mM.

The blood plasma level of ketone will depend on the body weight of the individual and we have found that oral administration of (R)-3-hydroxybutyrate-(R)-1,3-butanediol monoester of at least 300 mg per kilogram of body weight provides a blood plasma concentration of (R)-3-hydroxybutyrate of around 1.5 mM and administration at 500 mg/kg provides at least 3 mM (R)-3-hydroxybutyrate. At a dose of 1 g/kg of body weight of the subject, the blood (R)-3-hydroxybutyrate concentration is suitably at least 4 mM, preferably 5 mM. Upon oral administration of monoester of 1.5 g/kg of body weight of the subject, the blood (R)-3-hydroxybutyrate concentration is suitably at least 7 mM, preferably at least 8 mM, especially at least 9 mM. A dosing regime comprises multiple drinks consumed separately.

Blood levels of (R)-3-hydroxybutyrate may be determined by commercially available testing kits, for example, (R)-3-hydroxybutyrate can be measured on whole blood using a handheld monitor and reagent strips (Precision Xtra, Abbott Diabetes Care, UK).

The compound of the invention may be used to treat a healthy subject to reduce the effects of overtraining.

Compounds for use of the invention may be included with nutritional compositions. Suitably the nutritional composition comprises water and a source of (R)-3-hydroxybutyrate. Preferably, the composition comprises an ester of (R)-3-hydroxybutyrate, a flavouring and optionally one or more of a protein, carbohydrate, sugars, fat, fibre, vitamins and minerals. Suitably, the flavouring may comprise a fruit-based flavouring. In one embodiment, the flavouring is suitably bitter, for example coffee, chocolate, and cranberry. A bitter flavouring may be combined with other flavourings such as fruit based flavourings, for example grapefruit, raspberry and cranberry.

Compounds for use of the invention are preferably administered together with one or more carbohydrates and/or proteins and/or amino acids.

Compositions for use of the invention may comprise mixtures of isomers of the compounds defined herein.

The composition is suitably organoleptically acceptable. By "organoleptically acceptable" we mean that the composition must possess acceptable sensory properties of taste, colour, feel and odour.

The composition may comprise a mid-chain triglyceride (MCT). If present, the mid-chain triglyceride preferably comprises a mid-chain triglyceride having a formula $CH_2R_a$—$CH_2R_b$—$CH_2R_c$ wherein $R_a$, $R_b$ and $R_c$ are fatty acids having 5 to 12 carbon atoms. Suitably, $R_a$, $R_b$, and $R_c$ are fatty acids containing a six-carbon backbone (tri-C6:0) as tri-C6:0 MCTs are reported to be absorbed very rapidly by the gastrointestinal tract.

The composition of the invention may comprise L-carnitine or a derivative of L-carnitine. Examples of derivatives of L-carnitine include decanoylcarnitine, hexanoylcarnitine, caproylcarnitine, lauroylcarnitine, octanoylcarnitine, stearoylcarnitine, myristoylcarnitine, acetyl-L-carnitine, O-Acetyl-L-carnitine, and palmitoyl-L-carnitine. Where a carnitine is employed, suitably the composition of the invention comprises i) a ketone body, preferably a ketone monoester, more preferably a (R)-3-hydroxybutyrate monoester and ii) L-carnitine or a derivative of L-carnitine and optionally an MCT.

A suitable dosage of L-carnitine would be, for instance, 2 portions of 2000 mg L-carnitine-tartrate per day. The L-carnitine may be administered together with carbohydrates and/or protein. The L-carnitine may be administered for a relatively long period of time, for instance, 6 months or more.

Where MCT and L-carnitine or its derivative is employed, suitably the MCT is emulsified with the carnitine. Preferably 10 to 500 g of emulsified MCT is combined with 10 to 2000 mg of carnitine for example 50 g MCT (95% triC8:0) emulsified with 50 g of mono- and di-glycerides combined with 500 mg of L-carnitine. Preferably the level of the source of (R)-3-hydroxybutyrate is greater than the level of the MCT.

Compositions according to the invention may be provided in any suitable form, including a solid, for example a powder, tablet, bar, confectionary product or a granule, a liquid, for example a beverage, a gel, a capsule or any other conventional product form. The composition may be a food product, food supplement, dietary supplement, functional food or a nutraceutical or a component thereof.

Examples of food products into which the composition may be incorporated as an additive include snack bars, cereals, confectionery and probiotic formulations including yoghurts. Examples of beverages include soft beverages, alcoholic beverages, energy beverages, dry drink mixes, nutritional beverages and herbal teas for infusion or herbal blends for decoction in water.

A nutraceutical is a food ingredient, food supplement or food product, which is considered to provide a medical or health benefit, including the prevention and treatment of disease. In general, a nutraceutical is specifically adapted to confer a health benefit on the consumer. A nutraceutical typically comprises a micronutrient such as a vitamin, mineral, herb or phytochemical at a higher level than would be found in a corresponding regular food product. That level is typically selected to optimise the intended health benefit of the nutraceutical when taken either as a single serving or as part of a diet regimen or course of nutritional therapy.

The compound of the invention is typically formulated as a food or nutraceutical.

When in solid form, the composition suitably comprises at least 5% by weight of the compound of the invention, which is preferably an ester, more preferably at least 10% by weight and up to 95% by weight of the composition. Whilst a level of 15 to 30% by weight of a dry composition may be suitable, for example where the composition is a dry powder intended for use with a liquid to produce a liquid composition, a solid bar or product form suitably comprises from 30 to 95%, especially 50 to 95% by weight of the composition.

When the composition is in solid form the composition may further comprise one or more of the following components:
- a diluent for example lactose, dextrose, saccharose, cellulose, corn starch or potato starch;
- a lubricant for example silica, talc, stearic acid, magnesium or calcium stearate and/or polyethylene glycols;
- a binding agent for example starches, arabic gums, gelatin, methylcellulose, carboxymethylcellulose, or polyvinyl pyrrolidone;
- a disintegrating agent such as starch, alginic acid, alginates or sodium starch glycolate;
- an effervescing agent;
- a dyestuff;
- a flavouring;
- a wetting agent, for example lecithin, polysorbates, lauryl sulphates; and/or
- a carrier.

Where the composition is in liquid form, the composition suitably comprises a compound of the invention at a level of at least 1%, for example 3 to 40% by weight of the liquid composition, but may be higher, for example up to 50% by weight of the composition, depending on whether the composition is intended to be taken as a single dose or in multiple smaller doses to reach the desired blood ketone level.

The composition in liquid form may comprise several liquid components that are suitably blended together or may comprise liquid and solid components that are mixed with or dissolved in the liquid component as appropriate. In one embodiment, a dry composition comprising the ketone is diluted with a suitable liquid, for example water, fruit juice, yoghurt or milk, preferably at a ratio of 1:1 to 1:10, more preferably 1:3 to 1:7 of dry composition to liquid.

The composition may be provided, as desired, as a liquid product in a form ready for consumption or as a concentrate or paste suitable for dilution on use. The diluent for use with the liquid composition is preferably milk, fruit juice or water.

If desired, the composition may also be provided in encapsulated form, provided that the encapsulation material and the quantity in which it is used is suitable for safe human consumption.

The invention provides in further aspect a kit comprising a compound in accordance with the first aspect of the invention, preferably an ester, or a composition according to the invention, and a ketone monitor and optionally instructions as to the level of product to consume per unit body weight and a dosage regimen to prevent or treat overtraining. Suitably, the user consumes the product and may then periodically test their blood plasma ketone level to determine whether further ingestion of ketone is required to reach or to maintain a desired blood plasma ketone level.

One aspect of the invention provides compounds of the invention as defined above in a pharmaceutical composition, optionally together with one or more pharmaceutically acceptable excipients.

Compounds of the invention may be present as pharmaceutically acceptable salts. As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases such as alkyl amines, aralkyl amines and heterocyclic amines.

Compounds of the invention may be present as solvates. The term "solvate" refers to a complex or aggregate formed by one or more molecules of a solute, i.e. compounds of the invention or pharmaceutically-acceptable salts thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

The compounds of the invention contain a chiral center. Accordingly, they can be used in the form of a racemic mixture, an enantiomer, or a mixture enriched in one or more stereoisomer. The scope of the invention as described and claimed encompasses the racemic forms of the compounds of the invention as well as the individual enantiomers, and stereoisomer-enriched mixtures.

It will be appreciated that the term "or a pharmaceutically acceptable salt or solvate thereof" is intended to include all permutations of salts and solvates, such as solvates of pharmaceutically-acceptable salts of compounds of the invention.

The pharmaceutical composition of the invention comprises a compound of the invention optionally admixed with one or more pharmaceutically acceptable diluents, excipients or carriers. Even though the compounds of the present invention (including their pharmaceutically acceptable salts, esters and pharmaceutically acceptable solvates) can be administered alone, they will generally be administered in admixture with a pharmaceutical carrier, excipient or diluent, particularly for human therapy. The pharmaceutical compositions may be for human or animal usage in human and veterinary medicine.

Examples of such suitable excipients for the different forms of pharmaceutical compositions described herein may be found in the "Handbook of Pharmaceutical Excipients, $2^{nd}$ Edition, (1994), Edited by A Wade and P J Weller.

Compositions of the invention (both pharmaceutical and nutritional) may comprise an adsorbent that is pharmaceutically acceptable. Suitably the adsorbent adsorbs the compound of the invention in or on the adsorbent. Advantageously, the flavour of the compound (which may be aversive to taste) is experienced to a lesser degree by the user than would be experienced on consumption of the same composition without the adsorbent. Preferably the adsorbent comprises a lattice or voids capable of retaining the compound of the invention. Any adsorbents used or known for use in food products may be employed. Examples of suitable adsorbents include a polymer hydrogel, for example a polymer of a crosslinked polycarboxylate homopolymer or copolymer, a clathrate, a cyclic oligosaccharide, for example cyclodextrins, and milk powder. The adsorbent may be present at any desired level according to the particular formulation and may be from 5% to 80% by weight of the composition, for example from 10 to 50%.

Typically, the subject of the invention is a mammal, for instance, a human.

Typically, use of the invention involves administering compounds orally, parenterally or intravenously. Oral administration is preferred.

The present invention also provides a compound, as defined herein, in substantially pure form or in association with one or more pharmaceutically acceptable diluents or carriers for use in a method of preventing or treating overtraining in a subject.

As used herein, the term "substantially pure form" typically refers to a compound at a purity of 50% or greater, preferably 75% or greater, more preferably 90% or greater, even more preferably 95% or greater, and most preferably 99% or greater.

The invention is described by reference to the following non-limiting Example.

EXAMPLE

Effect of Ketones on Exercise-Induced Musculoskeletal and Hormonal Dysregulation Subjects Healthy male subjects (n=24) were recruited. The males were aged between 18 and 30 years old, were physically fit and regularly involved in physical activity and had good health status confirmed by medical screening.

Table 1 shows an overview of the study design (A) and familiarisation sessions (B).

TABLE 1A

STUDY DESIGN

| (−) 3 weeks | (−2) weeks | (−1) week | Pre-test week | 3 weeks supervised overload period | Post-test week |
|---|---|---|---|---|---|
| Sport medical screening | Familiarisation sessions | REST | Pre-test week | Training (6 days/week 12 sessions/week) Ketone ester or placebo (control) after each session and pre-sleep | Post-test week |

TABLE 1B

FAMILIARIZATION

| Day 1 | Day 2 | Day 3 | Day 4 | Day 5 | Day 6 | Day 7 |
|---|---|---|---|---|---|---|
| VO2 max test | REST | TT30 min W30 s | REST | TT30 min W30 s | REST | REST |

Cycling $TT_{30\,min}$ = 30 min Cycling Time-Trial;
$W_{30\,s}$ = 30 s all-out sprints.

A randomized placebo-controlled (ketone ester versus placebo) intervention study was performed. The study involved a pretest and a posttest with a 3-week training overload period in between (Table 1A). During this 3-week period, subjects received either ketone ester or an isocaloric placebo (long chain triglyceride) after each training session and 30 minutes before sleep. The conditions were blinded to both the subjects and the investigators until completion of all the experiments.

Three weeks prior to the start of the study, subjects underwent a sport medical screening by a certified sports physician. One week later, the subjects participated in three familiarization sessions (Table 1B) to get familiar with the experimental procedures. In the first familiarization session, the subjects performed a maximal incremental $VO_2$max test on a cycle ergometer (Avantronic Cyclus II, Leipzig, Germany). The initial workload was set at 60 W and increased by 30 W per min until volitional exhaustion. Respiratory gas exchange was measured continuously during the test (Cortex Metalyzer II, Leipzig, Germany), and the highest oxygen uptake measured over a 30-s period defined as the maximal oxygen uptake ($VO_2$max). Two days later, the subjects participated in a second and third familiarization session with a 48-h interval in between. In each of these sessions, they performed a 30-min simulated time trial ($TT_{30min}$) on the cycle ergometer. Following 15 min of active recovery (cycling @ 50 W), subjects performed a 30-s all-out sprint (W30 s), with cadence fixed at 100 rev·min$^{-1}$. Mean power output registered in the latter $TT_{30min}$ was used as the initial workload for the $TT_{30min}$ in the experimental sessions. Subjects were assigned to either of the two groups using a 1:1 (1 KE vs. 1 placebo) stratified, simple randomisation procedure using the following strata: $VO_2$ max, mean power output, as well as body mass and height. Randomisation was performed to ensure double blindness.

Pretest

The subjects were instructed to refrain from any strenuous physical activity for at least 48 h prior to the pretest. In order to avoid differences in initial muscle glycogen concentration between the pretest and posttest, the subjects received detailed dietary instructions. In addition, on the evening before each experimental session, the subjects received a standardized carbohydrate-rich meal (1500 kcal of which 70 E % carbohydrates, 20 E % protein, 10 E % fat). Next morning upon arrival in the laboratory they consumed a standardized carbohydrate-rich breakfast containing ~750 kcal (70 E % carbohydrates, 20 E % protein, 10 E % fat). Following breakfast, the subjects rested for two hours.

For the first experimental session, after a 10-min warming up (5 min at 100 W, plus 5 min at 150 W), the subjects performed a $TT_{30min}$. During the first 5 minutes (t0-t5), the workload was set equal to the mean power output achieved during the $TT_{30min}$ in the last familiarization session. From t5 to t25, the subjects adjusted the workload at 5-min intervals according to their subjective perception of fatigue. From t25 to t30, 1-min adjustments were allowed so as to be able to establish full exhaustion by the end of the TT. Immediately after completion of the TT, subjects (1) scored the rate of perceived exertion on a 15-point Borg scale and completed a gastrointestinal symptom questionnaire. Following 15 min of active recovery (cycling @ 50 W), subjects performed a $W_{30s}$. One day later, the subjects returned to the laboratory for the second experimental session. During this session a $VO_{2max}$ test was performed. Initial workload was set at 60 W and is increased by 30 W per min until volitional exhaustion or failure to maintain cadence >65 rpm.

3-Week Training Overload Period

Following the pre-test, participants were enrolled in a 3-week supervised and fully-controlled exercise training program. Each week of the training program consisted of six training days with an interval training in the morning and an endurance training in the evening, for a total of twelve training sessions per week (Table 2).

TABLE 2

Overview of the different training sessions during one week of the 3-week supervised overload period

| | Day 1 | Day 2 | Day 3 | Day 4 | Day 5 | Day 6 | Day 7 |
|---|---|---|---|---|---|---|---|
| AM | 4-6 × 30 sec MAX + 4 min recup | 5 × 6 min @85% VO$_2$max + 8 min recup | 4-6 × 30 sec MAX + 4 min recup | 5 × 6 min @85% VO$_2$max + 8 min recup | 4-6 × 30 sec MAX + 4 min recup | 5 × 6 min @85% VO$_2$max + 8 min recup | REST |
| PM | 150 min @65% VO$_2$max | 150 min @65% VO$_2$max | 150 min @65% VO$_2$max | 150 min @65% VO$_2$max | 150 min @65% VO$_2$max | 150 min @65% VO$_2$max | REST |

Each training session started with a standardized 10-min warming-up (5 min at 100 W, plus 5 min at 150 W), and ended with a 10-min cooling-down at 50 W. As shown in Table 2, the training following the warming-up consisted of either a high-intensity interval-training session (HIIT) involving 30-s maximal sprints followed by 4-min active recovery at 50 W (Mon, Wed, Fri), or a high-intensity intermittent endurance training session involving 5×6-min of cycling at high intensity blocks (85% VO$_2$max) followed by 8-min active recovery @ 50% of VO$_2$max (Tue, Thu, Sat). The number of maximal sprints in the HIIT sessions increased from 4 in week 1, to 5 in week 2 and 6 in the final week. Endurance sessions were performed in the evening and consisted of 150 min of cycling at 65% VO$_2$max. During the 3-week training period the subjects abstained from any exercise other than the exercise prescribed by the study protocol.

On day 12 of the training overload period, the AM training session was replaced by an experimental session identical to the first experimental session of the pretest. Briefly, subjects performed a $TT_{30min}$ immediately followed by completion of the 15-point Borg scale and a gastrointestinal symptom questionnaire. Following 15 min of active recovery (cycling @ 50 W), subjects performed a $W_{30s}$.

Post-Test

One day after the last training session of the 3-week training period, the subjects participated in the post-test, which was identical to the pre-test.

Follow-Up Sessions During Recovery

After the posttest the subjects were instructed to abstain from training for a week. After 3 and 7 days in this recovery period a number of measurements that were done in the pretest and the posttest were repeated.

Ketone and Placebo Supplements

Immediately following each training session and 30 min before sleep, subjects received a recovery drink (6D Recovery Shake, Medix, Oudenaarde, Belgium) containing 1 g carbohydrates per kg body weight, plus 0.35 g whey protein isolate per kg body weight. Additionally, subjects received 0.35 g per kg body weight of a ketone ester drink or an isocaloric placebo (PL; long chain triglycerides) as a separate drink to be ingested together with the carbohydrate/protein recovery drink. The ketone ester supplement (ΔG®) delivered pure D-β-hydroxybutyrate-R 1,3 butanediol monoester. These nutritional supplements have been extensively tested before (see for instance Cox et al; Cell Metab 24: 256-268, 2016).

Details of Measurements

Blood Samples

Blood samples (2×5 ml) were taken from an arm vein by use of the Venoject® system into BD Vacutainer® tubes. Samples were taken immediately before and 2 h after $TT_{30min}$ in the pre- and posttest, and in the fasted state at day 1, 4, 8, 11, 15 and 18 during the training-overload period. Plasma was immediately separated by centrifugation. Serum and plasma samples were used to evaluate chemical markers using High Sensitivity ELISA kits.

Furthermore, during $TT_{30min}$ small capillary blood samples (5 μl) were collected at 5-min time intervals via a small puncture in the earlobe. These microsamples were immediately analyzed for blood lactate concentration (Lactate Pro®, Arkray, Kyoto, Japan), blood glucose and βHB levels (GlucoMen Lx plus-meter with Lx glucose or Lx β-ketone strips, Menarini Diagnostics, Firenze, Italy).

Urine Samples

Total nocturnal urine (10 pm to 8 am) was collected during the night before each experimental session in flasks prepared with 10 ml hydrochloric acid. Urinary volume output was noted and an aliquot of the well-mixed samples was stored at −80° C. until assayed in a single run for noradrenaline concentration using a commercially available enzyme linked immunosorbent assay (ELISA) (BA E-5400, LDN, Nordhorn, Germany).

Results

The results are demonstrated in the accompanying figures.

FIG. 1 illustrates ketone (β-hydroxybutyrate) levels in blood samples taken before exercise, immediately after exercise and 30 minutes following ingestion of either a ketone ester or a placebo drink. Samples were taken on days 6, 13 and 20. Blood β-hydroxybutyrate levels are shown to be significantly higher following ingestion of the ketone ester drink. Ketone ester intake consistently elevated blood (R)-3-hydroxybutyrate to ~2-3 mmol/L 30 minutes post exercise.

Figure 2A:
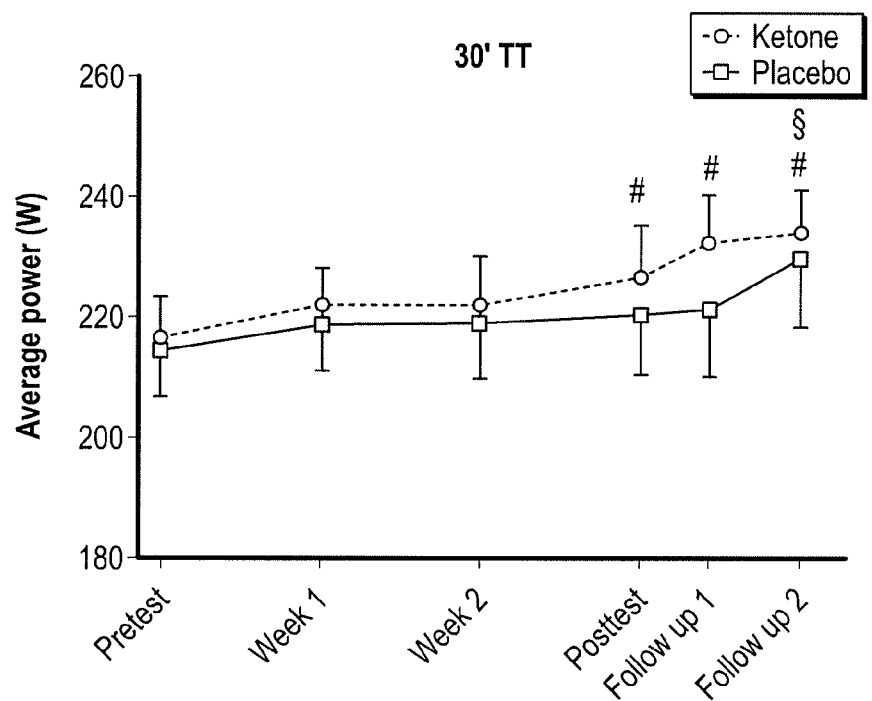
FIG. 2 shows average power output (FIG. 2A) and % increase in power compared with a placebo drink (FIG. 2B) during a 30-minute simulated cycling time trial.
Figure 2B:
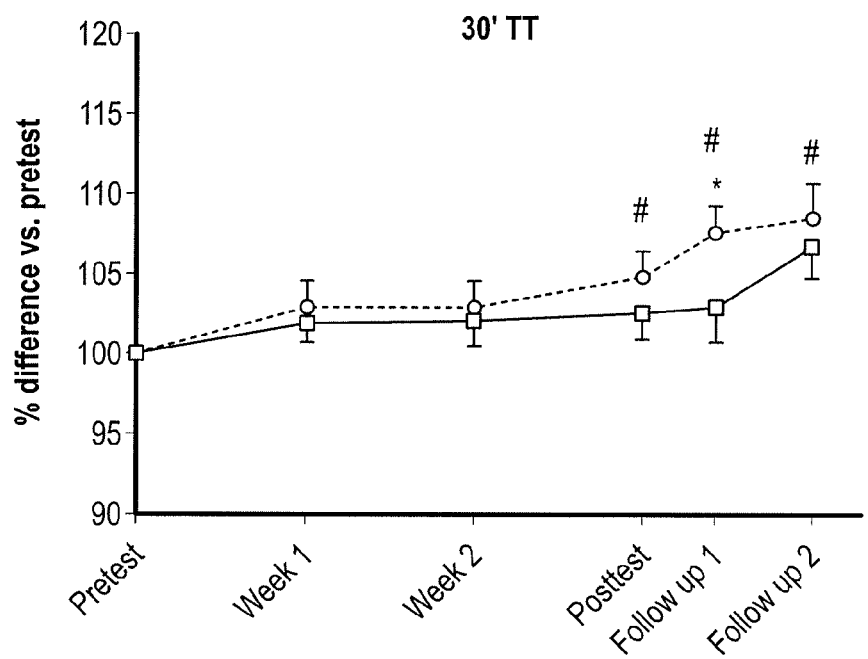

FIG. 2 shows the 30-minute time trial performances at different time points, from pre-test, weeks 1 and 2, post-test and follow-up sessions 3 and 7 days after the posttest, respectively. FIG. 2A shows the average power (W) during the 30 minute time trials, whereas FIG. 2B shows the increase, from pre-test values, in power during the 30 minute time trials. Average power was significantly higher at the post-test and follow-up 1 times for the ketone ester group. Following 1 week of tapering after a 3-week training overload period, power output was increased by ~8% in the ketone ester group, but not in the placebo group.

Figure 3:
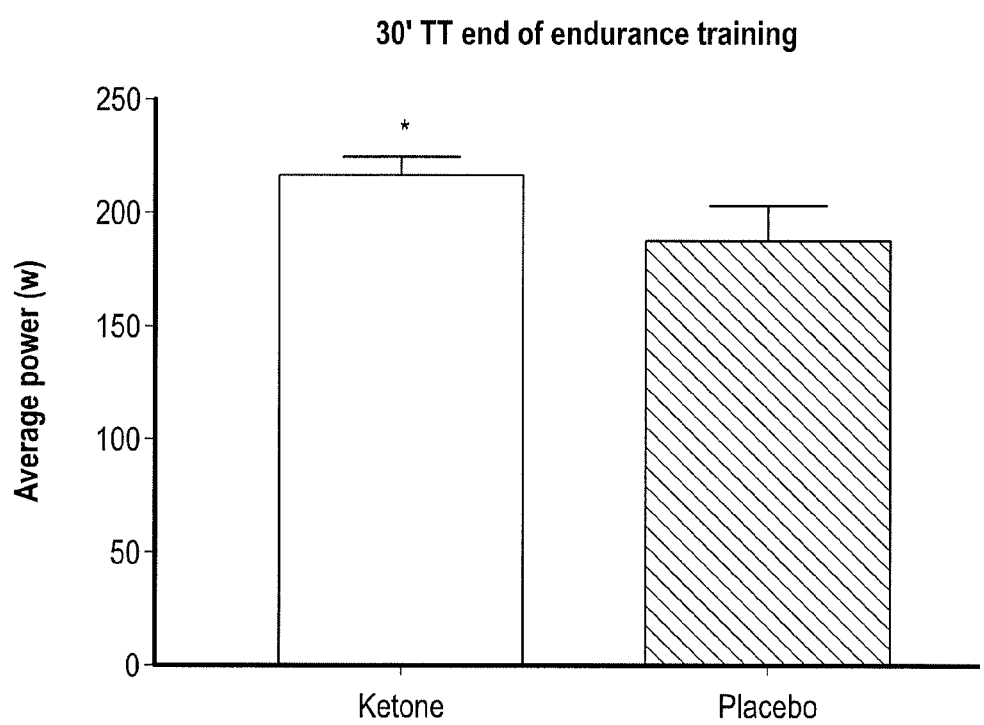
FIG. 3 shows mean power output during a 30-minute time trial immediately following a 2 h submaximal constant-load exercise bout at the end (day 18) of a 3-week training overload period.

FIG. 3 illustrates the 30 minute time trial performance results at the end of a 120 minute constant-load endurance training session at day 18 of the training period. Average power was significantly higher for the ketone ester vs. placebo group. Before training, performance was similar between the groups. However, on day 18 and compared with a placebo drink, ingestion of ketone ester increased mean power output by ~15%.

Figure 4A:
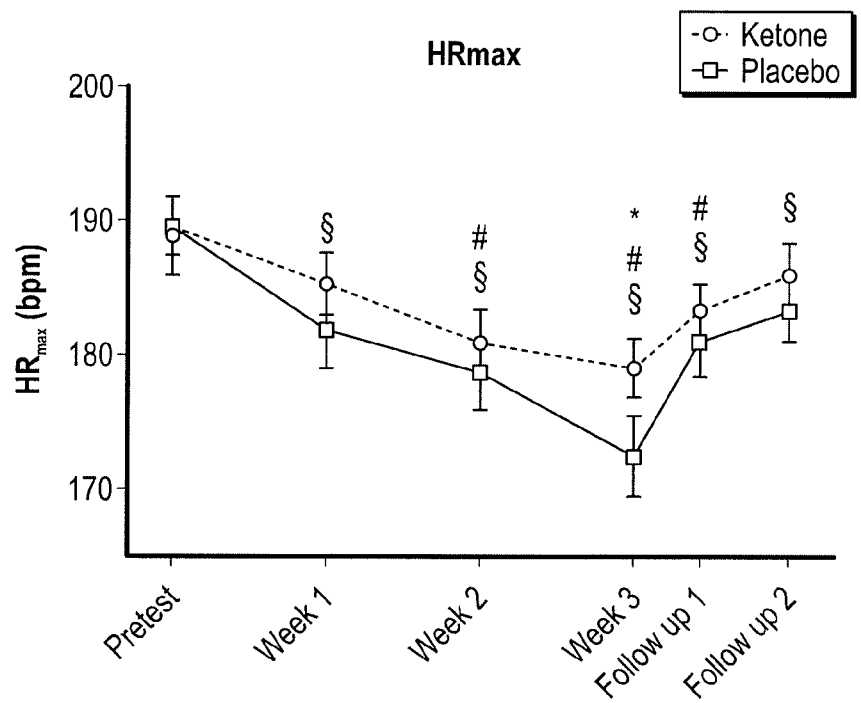
FIG. 4 shows the peak heart rate during a 90 second all-out isokinetic sprint (FIG. 4A shows the absolute values.
FIG. 4B shows the decline in heart rate versus the pre-test)
Figure 4B:
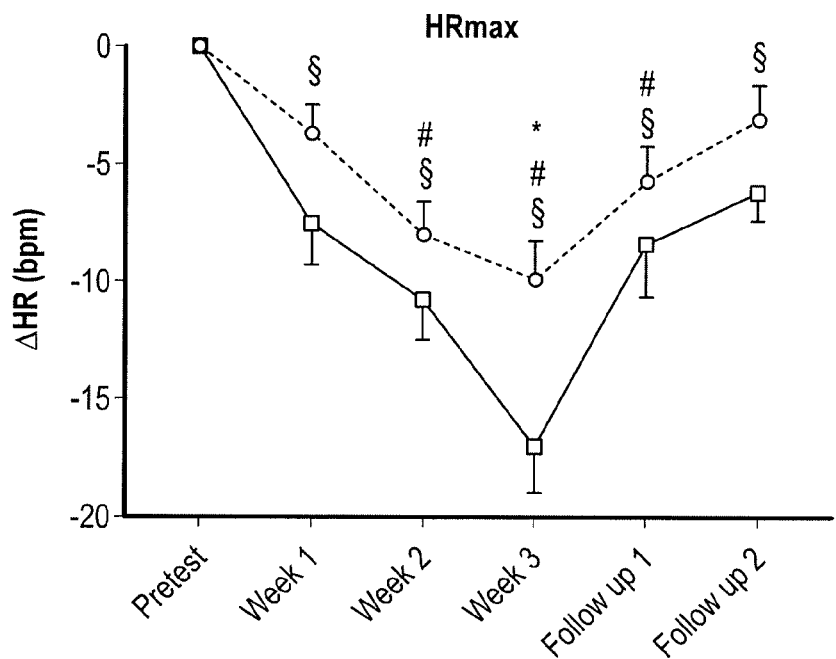

FIG. 4 shows the peak heart rate during 90 second all-out isokinetic sprints at different time points during the experiment. FIG. 4A gives the absolute values, and FIG. 4B gives the decrease in heart rate (Δ) from the pre-test values. During the experiment, there was a decline in maximum heart rate in all subjects, which was particularly marked by week 3 (and demonstrates that the subjects were suffering from overreaching/overtraining). However, the decline in maximum heart rate was significantly less for the subjects ingesting the ketone ester drink. Compared with a placebo drink, the decrement of maximal heart rate, which is a primary symptom of overreaching/overtraining, was inhibited by ketone ester intake during a 3-week training overload period.

Figure 5:
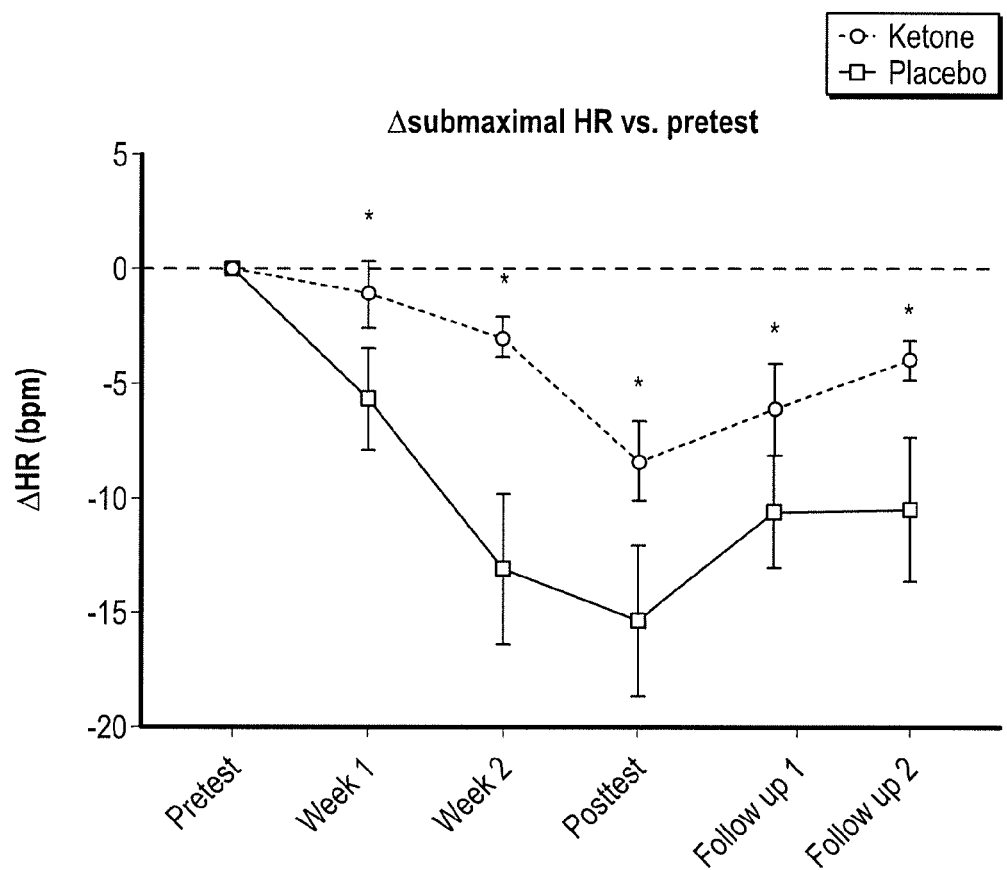
FIG. 5 shows the difference in submaximal heart rate measured during the first 5 minutes of a 30-min time trial compared to pre-test values.

FIG. 5 shows the change in the submaximal heart rates vs. the pre-test heart rates, which declined in all subjects during the experiment, but was significantly less in the ketone group. Decrease of heart rate for a given submaximal workload in well-trained individuals is a typical symptom of overtraining. Compared with a placebo drink, ketone ester intake inhibited the drop in submaximal heart rate during a 3-week training overload period.

Figures 6A, 6B, 6C:
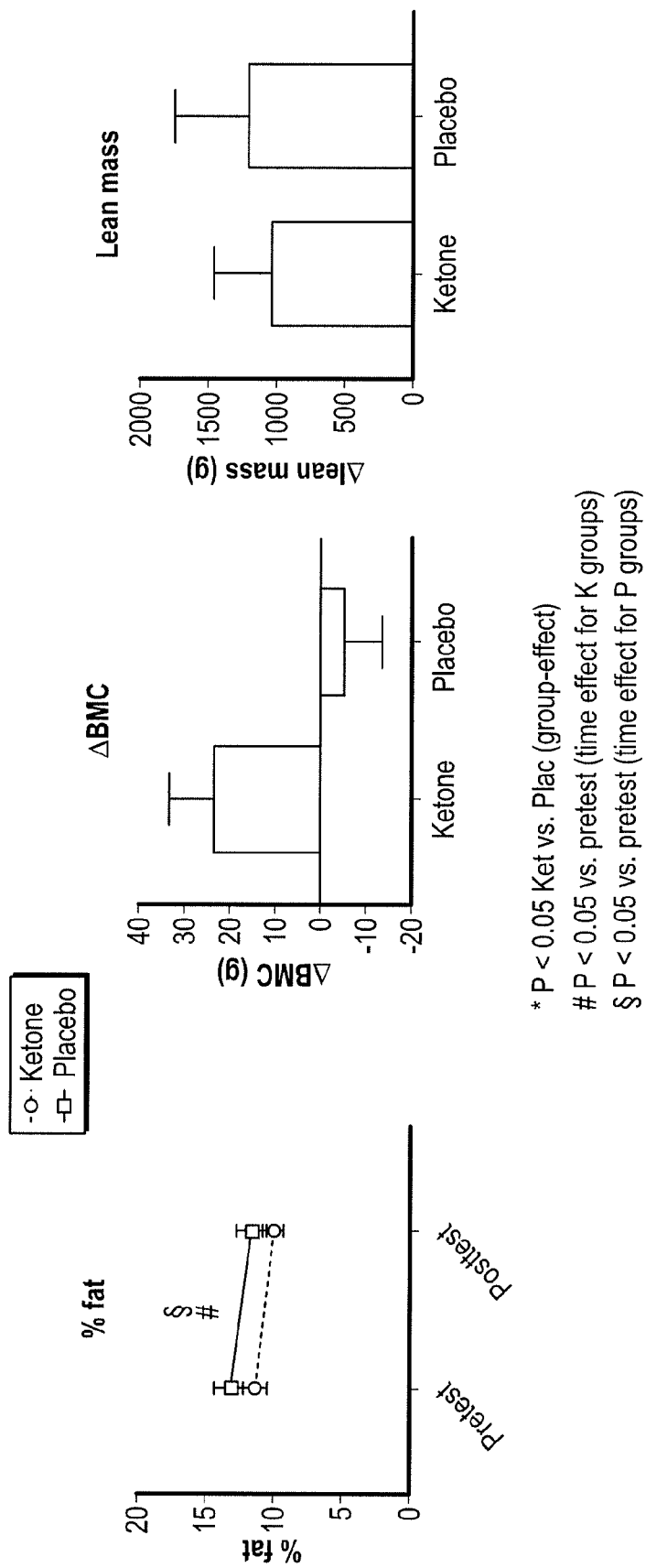
FIG. 6A shows the % fat.
FIG. 6B shows the change in bone mineral content and FIG. 6C shows the change in lean mass versus the pre-test.

FIG. 6 shows the results of DXA scans, pre- and post-test, on the % body fat (FIG. 6A), change in bone mineral content (FIG. 6B) and change in lean body mass (FIG. 6C). Percentage body fat decreased from the pre- to post test states for all subjects, as would be expected. The lean body mass increased to the same extent in both groups. Interestingly, subjects who drank the ketone ester had increased bone mineral content in the post-test compared to placebo (FIG. 6B). Loss of bone mineral mass is a typical symptom of endurance training overload, particularly in non weight-bearing sports such as cycling and swimming. Compared with placebo, ketone ester intake did not alter changes in body fat and lean body mass during a 3-week training overload period, yet increased bone mineral content.

Figure 7:
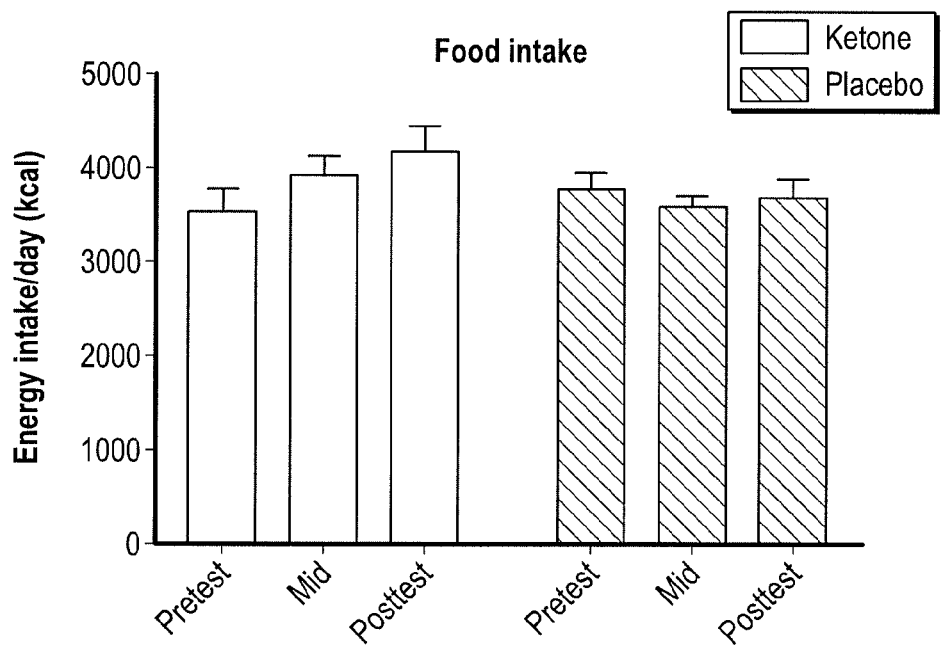
FIG. 7 shows the food intake in the ketone and placebo groups—energy intake was measured over two days at the beginning (pre-test), mid (mid) and end (post-test) of the three-week training period.

FIG. 7 shows that subjects on ketone ester spontaneously increased their energy intake as energy expenditure in training was increased from week 1 to week 3, whilst in placebo energy intake was stable. Training load was gradually increased during a 3-week training overload period. Opposite to subjects on placebo, subjects on ketone ester spontaneously increased their daily energy intake to compensate for increasing energy expenditure in training.

Figure 8:
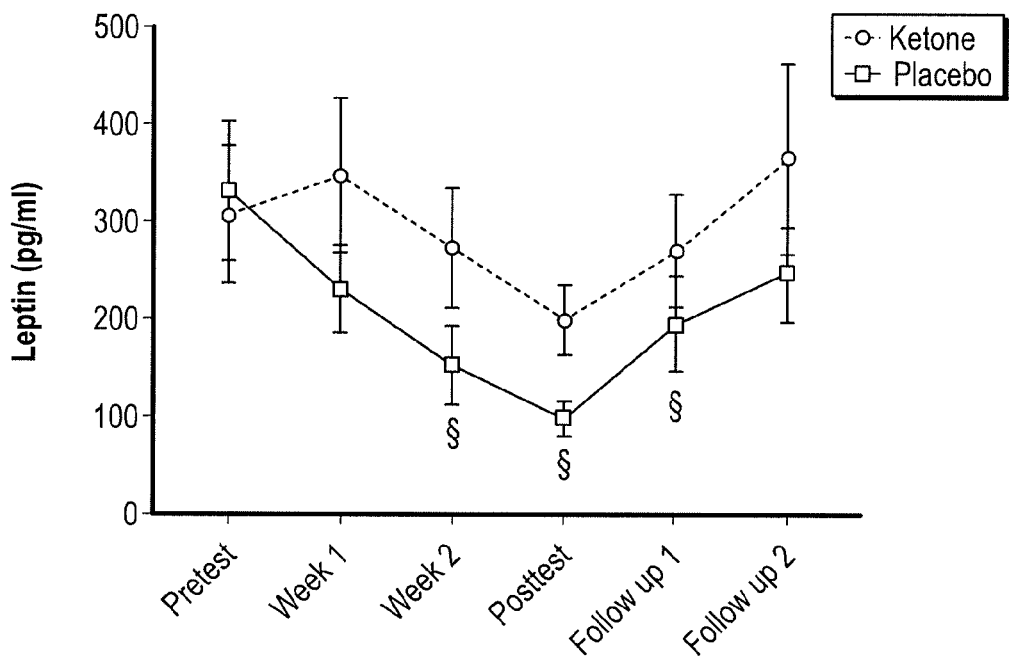
FIG. 8 shows leptin levels over time in fasted plasma samples.

FIG. 8 shows leptin levels over time. Leptin plays an important role in body weight and energy balance control. From the pretest to the posttest leptin levels significantly dropped in the placebo group, whilst they were constant in the ketone group. Leptin levels were higher at all timepoints after the pretest for the ketone ester group, compared to the placebo. This may indicate that ketone ester intake may contribute to maintain a hormonal milieu that facilitates to match energy intake to energy expenditure during episodes of strenuous training/overtraining.

Figure 9A:
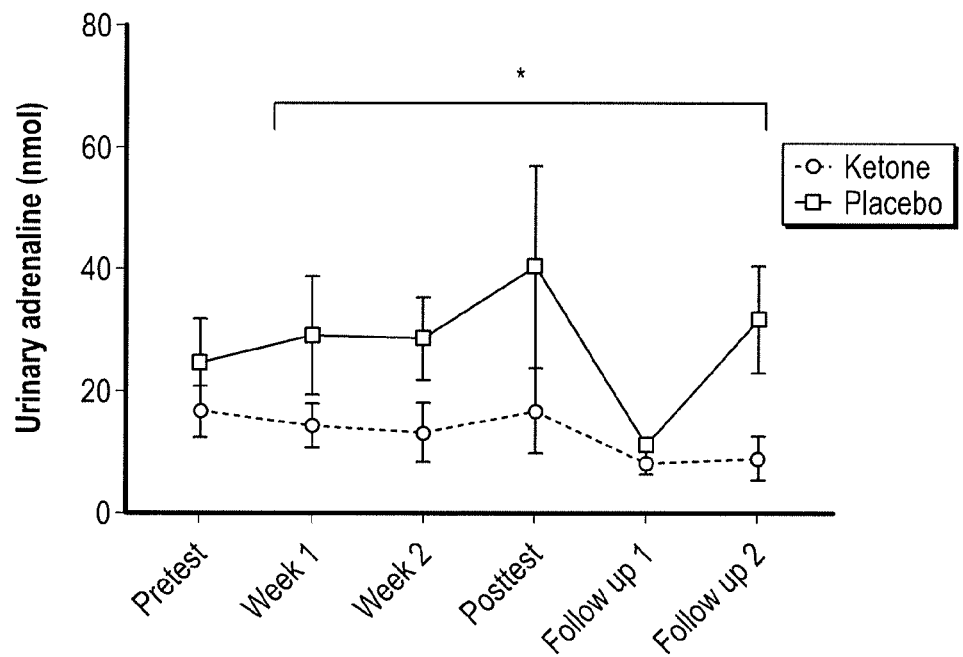
FIG. 9 shows urinary total nocturnal adrenaline—FIG. 9(a)—and noradrenaline—FIG. 9(b)—excretion before and during the 3-week overreaching/overtraining period.
Figure 9B:
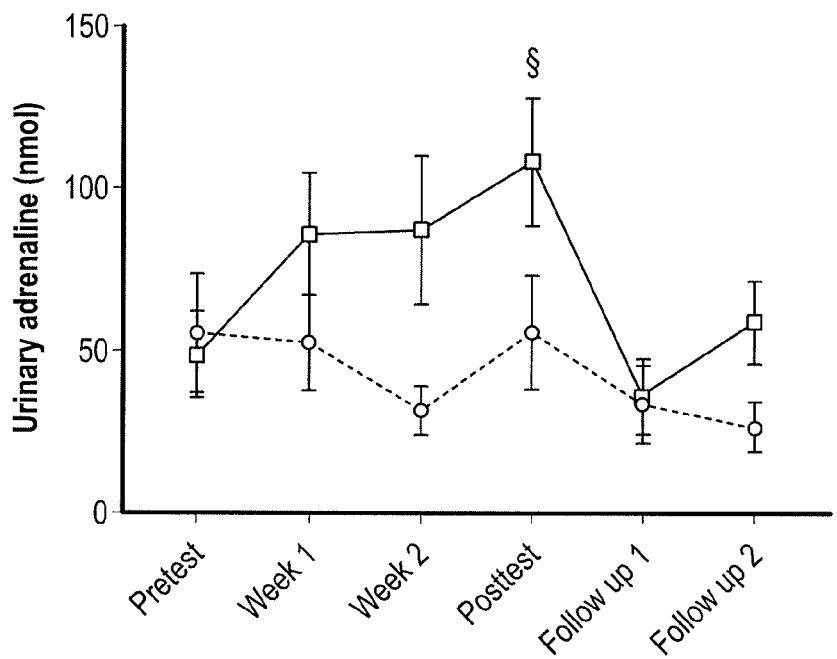

FIG. 9(b) shows urinary total nocturnal noraderenaline excretion before and during the 3-week overreaching/overtraining period. Noradrenaline excretion was consistently elevated in placebo, but was stable at baseline levels in the ketone group. This indicates that the overtraining programme increased sympathetic tone in placebo but not in subjects receiving ketones. FIG. 9(a) illustrates the results for adrenaline and shows a similar pattern.

Figure 10:
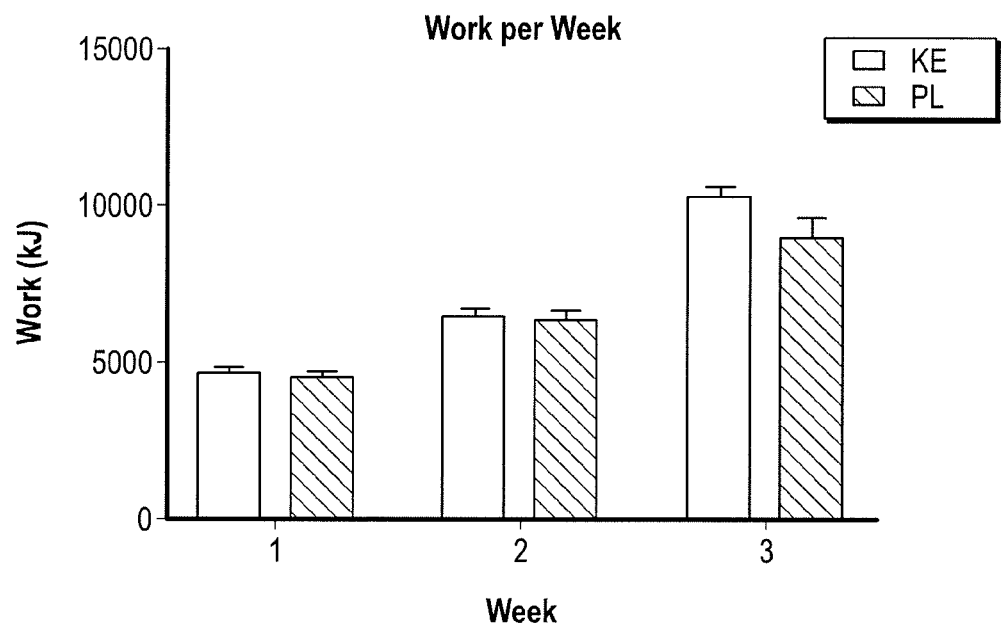
FIG. 10 shows training volume in work (kJ) per week of the ketone ester and placebo groups.
Figure 11:
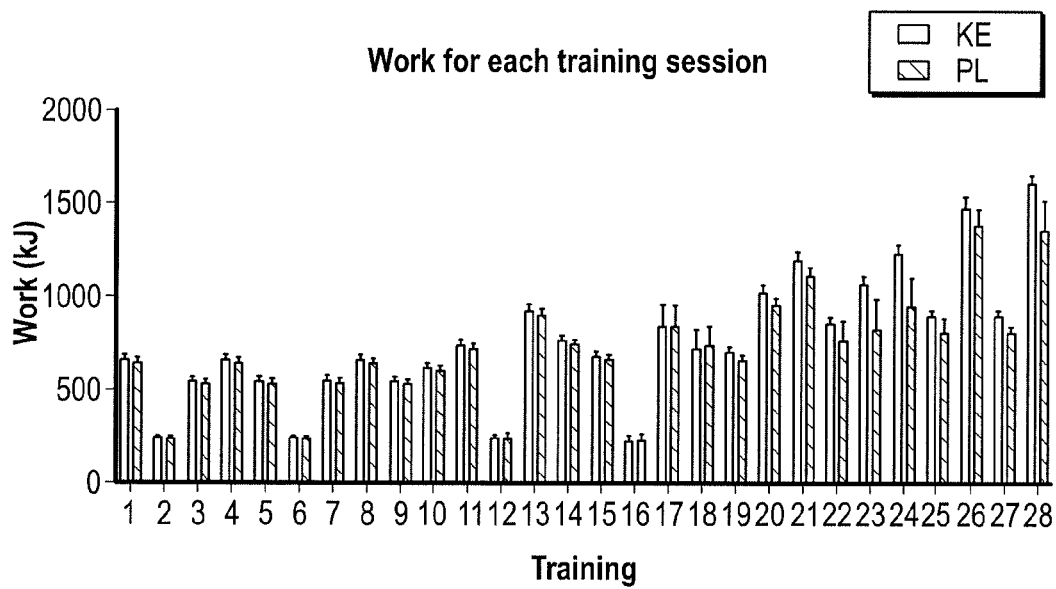
FIG. 11 shows the work for each training session for the ketone ester and ketone groups.

FIG. 10 shows work per week of the ketone ester and placebo groups, and FIG. 11 shows the work for each training session for the ketone ester and ketone groups. Regarding the training loads, there was no difference between the placebo and ketone groups in weeks 1 and 2, but by week 3 the training load was definitely higher in the ketone group than in placebo. In fact, from day 20 workload effected during each single training session was higher in the ketone group. Nonetheless, the ketone ester group was less overtrained by the end of the training period. Thus they were able to train more while developing less symptoms of fatigue and overreaching.

The invention claimed is:

1. A method of treating overtraining syndrome in a subject in need thereof, comprising administering to the subject an ester of (R)-3-hydroxybutyrate or a pharmaceutically acceptable salt or solvate thereof.

2. The method of claim 1, wherein the ester of (R)-3 hydroxybutyrate is a compound of general Formula I:

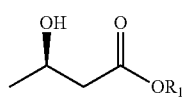

Formula I wherein:
$R_1$ is a $C_1$-$C_6$ alkyl group, which alkyl group carries up to five —$OR_2$ substituents, wherein $R_2$ represents hydrogen or a $C_1$-$C_6$ alkyl, or wherein —$OR_2$ represents a (R)-3-hydroxybutyrate moiety; or $R_1$ is a moiety derived from an alcohol ($HOR_1$), wherein said alcohol is a sugar.

3. The method of claim 2, wherein $R_1$ is a $C_1$-$C_6$ alkyl group substituted with 1, 2 or 3 —$OR_2$ substituents.

4. The method of claim 2, wherein $R_2$ is H.

5. The method of claim 2, wherein $R_1$ has the formula —$CH_2$—$CH(OH)$—$CH_2(OH)$ or —$CH_2$—$CH_2$—$CH(OH)$—$CH_3$.

6. The method of claim 2, wherein $R_1$ is the moiety derived from the alcohol ($HOR_1$), and the alcohol is a sugar selected from the group consisting of altrose, arabinose, dextrose, erythrose, fructose, galactose, glucose, gulose, idose, lactose, lyxose, mannose, ribose, ribulose, sucrose, talose, threose, xylose, and combinations thereof.

7. The method of claim 1, wherein the ester of (R)-3 hydroxybutyrate is (R)-3-hydroxybutyrate (R)-1,3-butanediol monoester of formula:

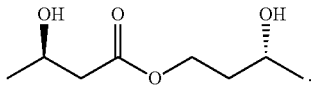

8. The method of claim 1, wherein the administering the compound to the subject treats one or more of the physiological, psychological, immunological or biochemical alterations associated with overtraining syndrome in the subject.

9. The method of claim 8, wherein treating overtraining syndrome in the subject comprises reducing, delaying or inhibiting the increase in noradrenaline levels associated with overtraining syndrome in the subject.

10. The method of claim 1, wherein treating overtraining syndrome in the subject comprises delaying the onset of symptoms of overtraining syndrome by at least one day.

11. The method of claim 1, wherein treating overtraining syndrome in the subject comprises reducing a loss of power associated with overtraining syndrome.

12. The method of claim 1, wherein treating overtraining syndrome in the subject comprises increasing or maintaining bone mineral content.

13. The method of claim 1, wherein the subject is an athlete or an endurance athlete.

14. The method of claim 1, wherein the administering comprises administering to the subject a pharmaceutical composition comprising the ester of (R)-3-hydroxybutyrate or a pharmaceutically acceptable salt or solvate thereof and optionally one or more pharmaceutically acceptable excipients.

15. The method of claim 1, wherein the administering comprises administering to the subject a nutritional composition comprising the ester of (R)-3-hydroxybutyrate or a phamaceutically acceptable salt or solvate thereof, optionally water, and optionally one or more of a flavouring, a protein, carbohydrate, sugars, fat, fibre, vitamins, and/or minerals.

16. The method of claim 15, wherein the nutritional composition further comprises a mid chain triglyceride.

17. The method of claim 16, wherein the mid chain triglyceride is represented by $CH_2R_a$—$CH_2R_b$—$CH_2R_c$ wherein $R_a$, $R_b$ and $R_c$ are fatty acids having 5 to 12 carbon atoms.

* * * * *

UNITED STATES PATENT AND TRADEMARK OFFICE
CERTIFICATE OF CORRECTION

PATENT NO. : 12,290,496 B2  
APPLICATION NO. : 17/282594  
DATED : May 6, 2025  
INVENTOR(S) : Kieran Clarke et al.

Page 1 of 1

It is certified that error appears in the above-identified patent and that said Letters Patent is hereby corrected as shown below:

In the Claims

Claim 14, Column 18, Line 51, "pharamaceutically" should read --pharmaceutically--.

Claim 15, Column 18, Line 57, "pharamaceutically" should read --pharmaceutically--.

Signed and Sealed this  
Sixteenth Day of September, 2025

Coke Morgan Stewart  
*Acting Director of the United States Patent and Trademark Office*